(12) United States Patent
Bentvelsen et al.

(10) Patent No.: US 6,291,746 B1
(45) Date of Patent: Sep. 18, 2001

(54) PLANT BREEDING

(75) Inventors: Gerardus Cornelius Maria Bentvelsen, Grootebroek; Henricus Godefriedus Wilhelmus Stemkens, Hoorn; Pieter Tjeertes, Enkhuizen, all of (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 07/999,172

(22) Filed: Dec. 28, 1992

Related U.S. Application Data

(63) Continuation of application No. 07/746,525, filed on Aug. 16, 1991, now abandoned, which is a continuation of application No. 07/402,583, filed on Sep. 1, 1989, now abandoned.

(30) Foreign Application Priority Data

Sep. 5, 1988 (GB) .................................................. 8820835

(51) Int. Cl.$^7$ ....................................................... A01H 5/00
(52) U.S. Cl. ......................... 800/311; 800/266; 800/271; Plt./87.12
(58) Field of Search ..................................... 800/200, 230, 800/208, 311, 266, 271; Plt./87.12; 438/240.4

(56) References Cited

U.S. PATENT DOCUMENTS

| P.P. 3,874 | * | 4/1976 | Duffett et al. | Plt./68 |
| P.P. 6,220 | * | 7/1988 | Craig | Plt./68 |
| P.P. 6,286 | * | 9/1988 | Gugino | Plt./68 |
| P.P. 6,605 | * | 2/1989 | Jacobsen | Plt./68 |

OTHER PUBLICATIONS

Horn et al. 1986 "Int. Symp. Eucorpia Breeding & Propagation of Ornamental plants" pp. 20–29.*
Gray 1967 *The Dictionary of the Biological Sciences* Rhinehold Publishing Corp NY p 487.
Allard 1960 *Principles of Plant Breeding* John Wiley & Sons NY p 14–15.
Martin et al. 1976 *Principles of Field Crop Production 3rd Ed* Macmillan Publ Co NY p 420 654, 852.
Soule 1985 *Glossary for Horticultural Crops* John Wiley and Sons NY p 322.

* cited by examiner

Primary Examiner—Gary Benzion
(74) Attorney, Agent, or Firm—Bruce Vrana

(57) ABSTRACT

Diploid *Pelargonium peltatum* plants containing a factor resulting in male sterility and/or in their petals at least one of the anthocyanidins pelargonidin and paeonidin, and which may be propagated by seed, as well as the introduction of said characteristics into *Pelargonium peltatum* using plant breeding and tissue culture techniques.

27 Claims, 3 Drawing Sheets

PLANT BREEDING

This is a continuation of application Ser. No. 07/746,525, filed Aug. 16, 1991, now abandoned, which is a continuation of application Ser. No. 07/402,583, filed Sep. 1, 1989, now abandoned.

The present invention utilises plant breeding and tissue culture techniques to introduce favourable characteristics into the pelargonium species *Pelargonium peltatum*.

BACKGROUND

In the agricultural market the aim of plant breeding is largely to increase the yield of the crops whereas in breeding of ornamental plants it is to produce new, different and attractive varieties. Whatever the final product, the goal of all breeders is to combine favourable characteristics of parent plants in the progeny.

Although Mendelian variation may result in the production of new/different characteristics and spontaneous mutations may result in the presence of sports, the most satisfactory method for the introduction of new characteristics is by carefully controlled breeding. With plants which are self-pollinating, this may take the form of pure-line selection, mass selection or hybridisation followed by handling of the segregating generations by a) pedigree method, b) bulk method or c) back cross method. These three methods are all based on the fact that selfing, or back-crossing to a homozygous parent leads to homozygosity, thus ensuring the presence of the traits in successive generations. With plants which are outbreeding self-pollination may occasionally be possible, but such usually results in a loss in vigour of the plants. Outbreeding plants may be bred using pure-line selection and hybridisation, with the later handling being the same as for the self-pollinated plants.

Back-crossing provides a precise way of improving varieties which are superior in a large number of characteristics and deficient in only a few. If such a method is employed in interspecific hybridisation, wherein the parent plants originate from different species, certain features of one species may be transferred to the other without impairing the taxonomic integrity. Thus one species may become enriched with characteristics originating from another.

There are often, however, problems associated with interspecific hybridisation. For example interspecific hybrids often suffer a loss of reproductive capacity with the result that $F_1$ and later generations demonstrate a greater or lesser extent of sterility. Such may be due to genetic or cytoplasmic incompatibilities which are demonstrated either by a failure in fertilisation or death of a zygote before maturity.

With regard to ornamental plants, and in particular the members of the highly popular Pelargonium genus, during interspecific hybridisation between some members of the Ciconium section, such as *P. acetosum, P. inquinans,* and *P. zonale,* and the sole species of the Dribrachya section, *P. peltatum,* even though fertilisation may be accomplished, fully developed seeds have not resulted [Yu, Sun Nam (1985) Diss. Institut für Landwirtschaftlichen und G artnerischen Pflanzenbau, Weihenstephan]. Thus production of a fertile *Pelargonium peltatum* plant capable of being propagated by seed and illustrating a combination of the characteristics of the parent species, or the transfer of characteristics of one species to *Pelargonium peltatum* to produce such a fertile, seed propagatable plant, has thus far not been possible at the diploid level.

The genus Pelargonium belongs to the vegetable family Geraniaceae and is divided into 14 sections totalling approximately 280 species. Members of the Pelargonium genus are normally protandrous, i.e. the pollen develops before the stamen, and thus cross-pollination is the norm. An enormous variety of characteristics is encompassed by the members of the genus with plants ranging from trawling or hanging species to compact shrubs, from those with large and abundant flowers to others which produce few delicate flowers. The plants themselves are extremely popular with the public, being easy to care for and inevitably producing flowers of brilliant colour.

The present invention is largely concerned with the introduction of new reproducible traits into the species *Pelargonium peltatum*. The colours obtainable in the flowers of botanical species are predominantly shades of palish pink, lavender, mauve and sometimes whitish. Although scarlet, red, salmon and rose colours have been produced in some *Pelargonium peltatum* varieties, at both the diploid and tetraploid level, this plant material has a low fertility at the tetraploid level and is completely sterile at the diploid level. The presence of the genes resulting in these colours is probably the result of an interspecific hybridisation. Zehner et al (1981 Research Report Michigan State University) have shown that it is these colours which are most favoured by the public in pelargoniums and thus it would be economically advantageous to be able to produce such colouration in plants which are diploid, fertile and may be propagated by seed.

Due to the hermaphroditic nature of the botanical pelargonium plants, any plant may be selected as either the male or the female parent. In $F_1$ hybrid seed production in a number of horticultural crops, pollination is normally accomplished by hand. However, in order to ensure that the proper cross is made between the desired male and female plants, it is often necessary to remove the male reproductive parts from the plant such that pollen from the female does not self-pollinate or pollinate a sibling female plant. Such physical removal of the anthers is understandably labour-intensive and costly. In Pelargoniums, genetic male sterility (which is caused by a defect in or absence of the required nuclear genes) in a female fertile plant is known in the species *Pelargonium x hortorum* of the section Ciconium. Such sterility is characterised by the absence of stamen—the male reproductive organs—but the presence of a complete female reproductive capacity. Cytoplasmic sterility, caused by the absence of both the fertility genes in the cytoplasm and the fertility restorer genes in the nucleus, is also known in some *Pelargonium x hortorum* varieties. Cytoplasmic male sterility is preferred by plant breeders, as its presence enables 100% of the motherline, compared with 50% of the genetic male sterile motherline, to be used for seed production. Further, with cytoplasmic male sterility it is possible to produce an $F_1$ hybrid which is 100% male sterile. These male sterile plants are expected to produce flowers in more abundance than male fertile plants. Thus it would clearly be advantageous to plant breeders to have the feature of male sterility, and preferably cytoplasmic male sterility, in *P. peltatum* plants.

The diploid character (in *P. peltatum* 2N=18) is most favoured by plant breeders due to problems inherent in the propagation by seed of tetraploid material which is both genetically and cytologically more complex. The assurance of fertility in $F_1$ and further generations produced from tetraploid parents can not be absolute with problems possibly being attributable to unequal segregation of chromosomes at meiosis, partial multivalent formation or lagging of chromosomes. Further, to reach a sufficient level of homozygosity in a tetraploid plant requires considerably more generations and it is thus preferable to use diploid material in such breeding programmes.

SUMMARY

The present invention overcomes the problems of introducing favourable characteristics into fertile plants of the diploid species *Pelargonium peltatum* which may be propagated by seed, by use of plant breeding and tissue culture techniques.

The favourable characteristics apparent in the plants of the invention include a broad flower colour range and male sterility and may also include the characteristics of abundant flowering, day-neutrality, broad petals and a white spot in the centre of the flower.

Figure 1:
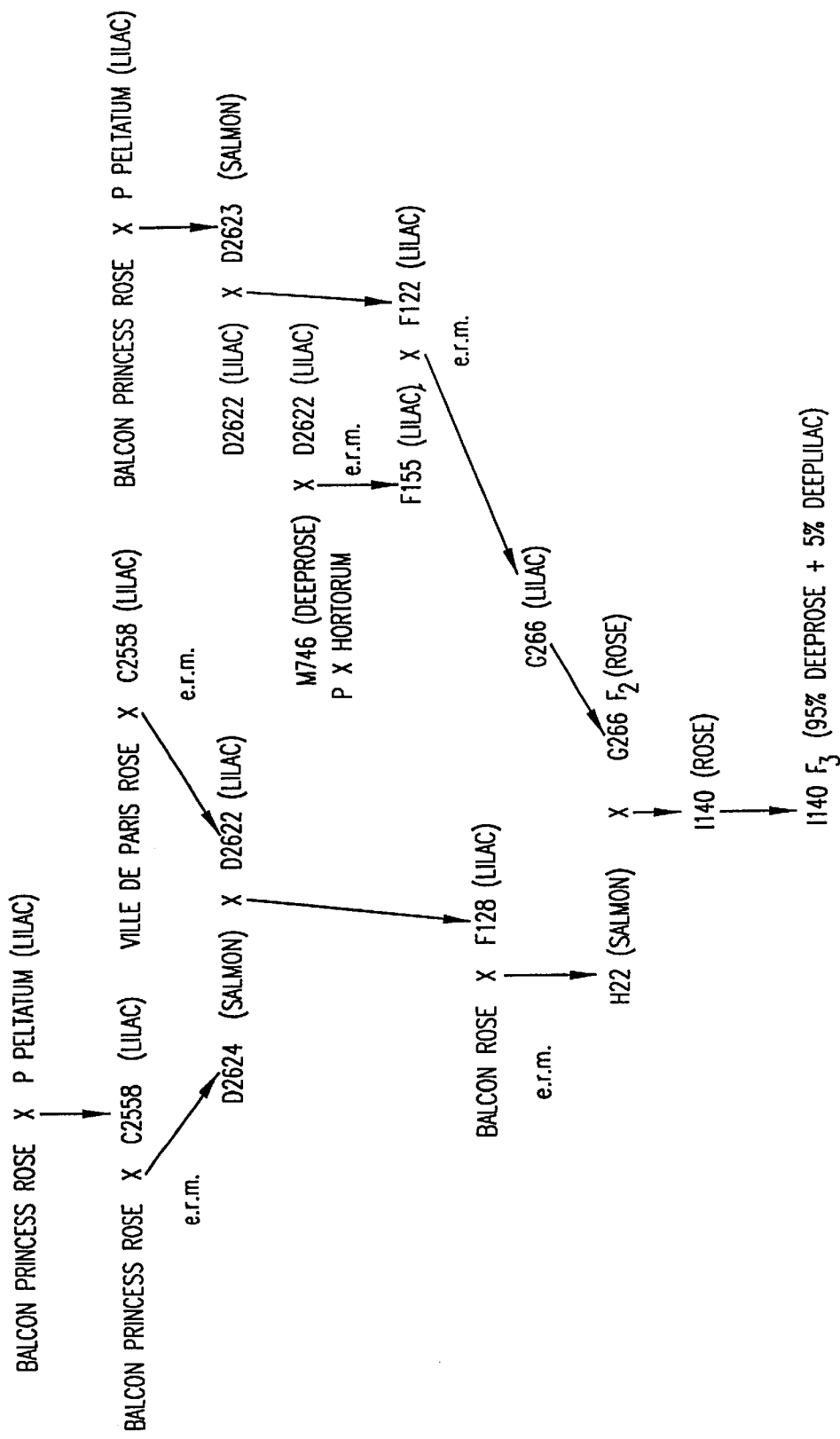
FIG. 1 shows an example of a breeding programme initiated to introduce rose colouring into the flowers of *Pelargonium peltatum*. The resulting plants, I140 may be subjected to self-pollination and would produce a uniform line for deep-rose. Plants produced in the breeding programme are numbered according to the year of their production. Genetic material for the Balcon Princess, *Pelargonium peltatum*, Ville de Paris and *Pelargonium x hortorum* is commercially available or available from botanical gardens.

In all of the crossing schemes illustrated in the figures, the plant on the right hand side of each cross is the male parent.

DETAILED DESCRIPTION

According to the present invention there is described a method for generating diploid *Pelargonium peltatum* plants (hereinafter also referred to as *P. peltatum*) containing at least one of the anthocyandins pelargonidin and paeonidin in the petals and/or a factor for male sterility, which plants may be propagated by seed, comprising:
    a) performing an initial cross wherein the genetic material of one parent is provided by *Pelargonium peltatum* and that of the other is selected from the group consisting of:
        i) *P. x hortorum*
        ii) *P. scandens*
        iii) a cascade type pelargonium
    b) selecting the progeny of (a) and subjecting it to further crosses with genetic material provided by a member of the group consisting of:
        i) *P. x hortorum*
        ii) *P. scandens*
        iii) a cascade type pelargonium
        iv) a plant produced according to (a)
        v) a plant produced in a breeding programme wherein the initial genetic material was provided by *Pelargonium peltatum* and one of *P. x hortorum*, *P. scandens* or a cascade type pelargonium, wherein at any stage in the breeding programme a plant displaying the desired characteristics may be selected for self-pollination such that a uniform line is produced;

said method involving circumvention of spontaneous early embryo abortion by removal of any fruit showing symptoms of such, and the in vitro cultivation of the embryo excised therefrom into differentiated plantlets.

The term "cascade type pelargonium" as used herein describes pelargonium plants such as, for example, Ville de Paris, Balcon Princess, Balcon, Decora and Cascade. It is, however, to be appreciated that the names given to such varieties vary according to the source of the material, and thus the term also encompasses those plants whose names are synonymous with those detailed above, the plants described by the term being characterised by the presence of male sterility, very low female fertility, i.e. practically female sterile, abundant flowering, narrow petals, the presence of the anthocyandins pelargonidin and paeonidin in the petals and the diploid number of chromosomes.

Also encompassed by the invention are diploid *Pelargonium peltatum* plants possessing such characters and genetic material, propagating material and seeds of such plants.

The introduction of the characteristics of broad petals, day-neutrality, abundant flowering and a white spot in the centre of the flower and plants containing such characteristics, is also an embodiment of the present invention. Most preferred in the plants of the invention are the characteristics of day-neutrality and a white spot in the centre of the flower. By day-neutrality is meant that the time of flowering of the plants is independent of the length of daylight.

The production of colour in the flowers of Pelargonium species is the result of the presence of pigments termed anthocyanidins. As used in this invention, this term describes the form in which the compounds are found in nature, ie in the form of glycosides. In the genus Pelargonium there are five naturally occurring anthocyanidins; malvidin, delfinidin, cyanidin, pelargonidin and paeonidin, not all of which are found in every species of the genus. For example, the flowers of commercially available *P. peltatum* species contain no pelargonidin or paeonidin and this explains the absence of the rose-scarlet-salmon shades in the botanical species, for it is these two pigments, in combination with the others, which are responsible for the production of shades within this range. It has been shown however that these two pigments are present in some species of the section Ciconium and in particular, in the species *P. x hortorum*. Further, *P. scandens,* also from the section Ciconium, contains genes which encode pigments resulting in salmon shades, and shades of salmon rose and scarlet are also found in cascade type pelargoniums.

Genetic male sterility, the introduction of which into *Pelargonium peltatum* also being an embodiment of the present invention, is known in certain seed propagated varieties of *Pelargonium x hortorum*. Cytoplasmic male sterility is also known in a vegetatively propagatable variety of *Pelargonium x hortorum*. Such male sterile plants may obviously only be used as a female parent in breeding programmes.

Cascade type pelargoniums are completely sterile and are normally only vegetatively propagated. However, Horn et al, [Luzny, J (ed), Eucarpia Meeting on Breeding and Propagation of Ornamental Plants, (1986) 20–29] have shown that at a low frequency such plants may be cross pollinated and will produce seeds. They were, however, unable to produce any viable $F_1$ plants from such crosses. The use of the method of the present invention has enabled viable $F_1$ plants to be produced when the genetic material of such cascade type pelargoniums is employed in the crossings.

The selection of plants to be used in the breeding programme is decided either by the visual demonstration by the plants of certain characteristics, i.e. is dependent on the plants phenotype, or by the demonstration of the presence of specific genes, i.e. is dependent on the plants genotype. In general it is sufficient for parents to be selected on the basis of phenotype.

All plants envisaged for use in this invention contain the diploid number of chromosomes.

Breeding programmes may be initiated and followed with the aim either of introducing colour into *P. peltatum,* or of introducing both colour and male sterility in the same programme. Further, it is possible to complete a programme designed to introduce desired colours into *P. peltatum* and to employ plants of this line in a programme to introduce male sterility. Thus the end products will contain both the desired colours and a factor for male sterility.

Plants involved in the breeding programmes are grown under normal cultivating conditions. Upon flowering, anthers are removed from male fertile plants to prevent inadvertent self-pollination and undesirable crosses. The desired crosses are achieved by hand pollination and the resulting seeds either left to develop in planta or, if the fruit displays signs of spontaneous early embryo abortion, the developing embryos are removed and cultivated in vitro. This so-called embryo rescue method involves the aseptic removal of the developing embryo from the ovaries approximately ten to fourteen days after the cross pollination, for example when the fruit shows a yellow colouring, and raising by incubation on agar. The embryos treated in this manner will differentiate roots and shoots and may then be transplanted into soil. The embryo rescue technique is described in more detail in Example 1.

Detection of successful introduction of the desired characters may be made either visually, for example male sterile plants will produce no stamen, or, in the case of petal colour, may also be by chemical means [Harborne, J CHROMATOGRAPHY 1 (1958) 473–488]. Thus to demonstrate the presence of the anthocyanidins in the petals, petal extracts are subjected to thin layer chromatography. The anthocyanidins may readily be distinguished by the different distances they travel along the cellulose support during the chromatography. The chromatography process is described in Example 3, and Table 1 shows the results of such on the extracts of petals from plants produced at various stages of the breeding programme. These results demonstrate the successful transfer of the genes resulting in pelargonidin and paeonidin production into these plants. In preferred *P. peltatum* plants of the invention at least 1%, more preferably at least 5%, particularly at least 10%, most preferably at least 25% of the anthocyanidins present in the petals are selected from pelargonidin and paeonidin.

In the method of the present invention, the choice of plant as male or female is dependent on the presence or absence of factors for male sterility. Where both parent plants are male and female fertile, either of the plants may be used as male or female.

To produce diploid *Pelargonium peltatum* plants possessing the characteristics of broad flower colour range and optionally the other characteristics of day-neutrality and a white spot in the centre of the flower, the parents of the first cross of the breeding programme are suitably selected from botanical *Pelargonium peltatum* and a cascade type pelargonium. It was found to be most suitable to use Balcon Princess as the cascade type pelargonium, although other cascade type pelargoniums are expected to behave in the same manner and may thus also suitably be used.

The progeny of the initial cross may be treated in various ways, depending i.a. on the phenotype of the progeny and the aim of the breeding programme.

Thus the progeny of the initial cross may follow any one of the paths outlined below:

1) It may be crossed with either of its parents. Such would be a back cross and would have the effect of enriching the characteristics of that parent in the next generation.
2) It may be crossed with a plant of the same section or group as one of its parents, either to introduce new characters or to affirm certain characteristics of that group.
3) It may be crossed with a plant from a section or group different from those of either of its parents. Such would have the effect of introducing further new characteristics.
4) It may be crossed with a plant which is itself the product of one or more crosses.
5) On rare occasions it may be self-pollinated thus establishing uniformity and eventually homozygosity within the plant.

Such breeding programmes are cumulative and span a number of years, with careful selection taking place at each stage of the programme.

The above disclosure generally describes the present invention. A more complete understanding can be obtained by reference to the following specific examples which are provided herein for purposes of illustration only, and are not intended to limit the scope of the invention.

EXAMPLE 1

Embryo Rescue Technique

Ten to fourteen days after cross pollination, ovaries showing signs of growth, ie the fruit begin to swell at the base and show a yellow colouring, were harvested and disinfected by rinsing for 2 minutes in 70% alcohol, followed by rinsing for 5 minutes in sterile demi water. The developing seed was then removed under a dissecting (low magnification) microscope in a sterile laminar air flow cabinet, and the embryo removed from the seedcoat.

The embryos were then incubated on Whites Agar Medium supplemented with 10% (w/v) coconut milk (Table A). After one week the embryos were transferred to Nitsch's Medium supplemented with 15% (w/v) coconut milk (Table A), and then transferred to fresh Nitsch's medium every week and maintained at 24° C. with a 16 hour photoperiod (±2000 Lux), until differentiation of leaves, stems and roots occurred. Once sufficient roots had formed the embryos were transplanted into soil and maintained in a greenhouse under plastic film in a high relative humidity (90–100%). After one week the plastic film was removed and the plantlets exposed to a lower RH of 40 to 80%. The temperature of the greenhouse is not vital and may vary within the range 15° to 25° C.

The average survival rate, ie development into plants from rescued embryos is approximately 32%.

TABLE A

| | WHITE'S MEDIUM | |
|---|---|---|
| Macronutrients | $KNO_3$ | 80 mg/l |
| | $Ca(NO_3)_2.4H_2O$ | 300 mg/l |
| | $MgSO_4.7H_2O$ | 720 mg/l |
| | KCl | 65 mg/l |
| | $NaH_2PO_4.H_2O$ | 16.5 mg/l |
| | $Na_2SO_4$ | 200 mg/l |
| Micronutrients | $MnSO_4.4H_2O$ | 7 mg/l |
| | $ZnSO_4.7H_2O$ | 3 mg/l |
| | $H_3BO_3$ | 1.5 mg/l |
| | KI | 0.75 mg/l |
| | $Fe(SO_4)_3$ | 2.5 mg/l |
| Amino Acids | glycine | 3 mg/l |
| | cysteine | 1 mg/l |
| Vitamins | pyridoxine HCl (B6) | 0.1 mg/l |
| | nicotinic acid | 0.5 mg/l |
| | thiamine HCl (B1) | 0.1 mg/l |
| | Ca D panthothenic acid | 1 mg/l |
| | coconut milk | 100 ml/l |
| | sucrose | 40 g/l |
| | agar | 8 g/l | pH 5.7–5.8 prior to autoclaving and prior to addition of agar.

| | NITSCH'S MEDIUM | |
|---|---|---|
| Macronutrients | $KNO_3$ | 950 mg/l |
| | $NH_4NO_3$ | 720 mg/l |
| | $CaCl_2.2H_2O$ | 220 mg/l |
| | $MgSO_4.7H_2O$ | 185 mg/l |
| | $KH_2PO_4$ | 68 mg/l |
| Micronutrients | $MnSO_4.4H_2O$ | 25 mg/l |
| | $ZnSO_4.7H_2O$ | 10 mg/l |
| | $H_3BO_3$ | 10 mg/l |
| | $CuSO_4.5H_2O$ | 0.025 mg/l |
| | $Na_2MoO_4.2H_2O$ | 0.25 mg/l |
| Amino Acids | glycine | 2 mg/l |
| Vitamins | myo-inositol | 100 mg/l |
| | pyridoxine HCl (B6) | 0.5 mg/l |
| | nicotinic acid | 5 mg/l |
| | biotin | 0.05 mg/l |
| | coconut milk | 150 ml/l |

-continued

| NITSCH'S MEDIUM | |
|---|---|
| sucrose | 40 g/l |
| agar | 8 g/l | pH 5.7–5.8 prior to autoclaving and addition of agar.

EXAMPLE 2

Production of Salmon Coloured Flowers in *P. peltatum*

The parents of the breeding programme to produce *P. peltatum* with salmon coloured flowers were chosen to be Balcon Princess, and *P. peltatum* plants demonstrating either white or lilac flowers. At a low frequency seeds were produced by these crosses and developed in the normal natural fashion. The resulting $F_1$ progeny, B2562 and C2258, displayed respectively salmon and lilac flowers and were themselves crossed. The zygotes resulting from this cross had to be removed from the plant and grown in culture (as per Example 1). Some of the $F_1$ progeny of this cross demonstrated the desired shade of salmon and were selected for self-pollination (see Breeding Scheme 1).

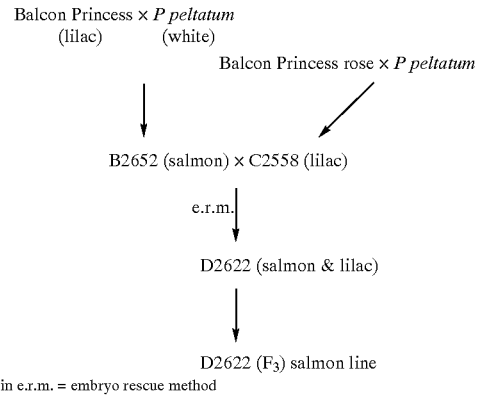

Breeding Scheme 1 wherein e.r.m. = embryo rescue method

Figure 2:
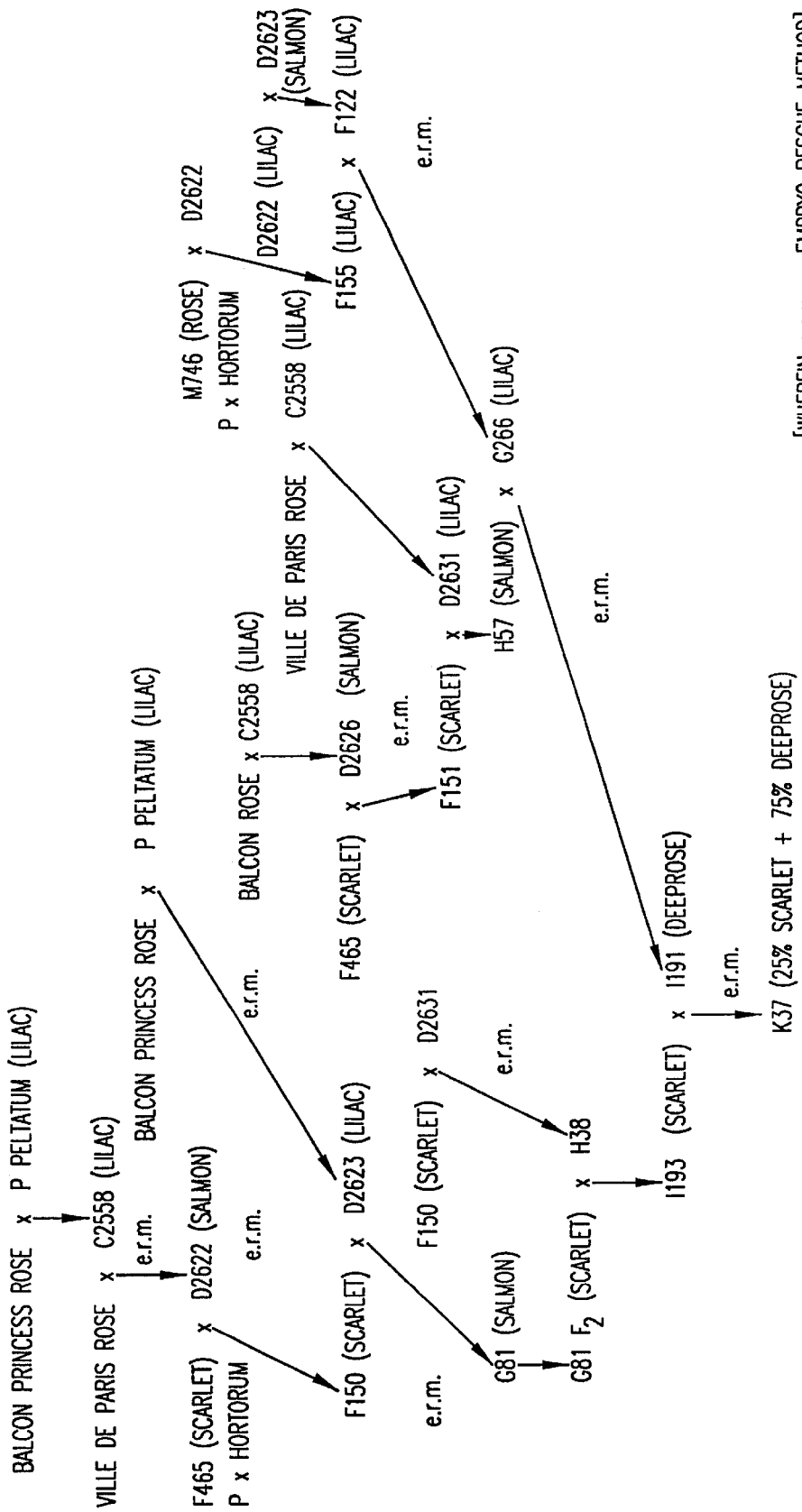
FIG. 2 shows an example of a breeding programme to introduce deep-rose and scarlet colouring into the flowers of *Pelargonium peltatum*. Uniform lines for each of these colours may be produced by self-pollination of K37. Genetic material for the Balcon Princess, *Pelargonium peltatum*, Ville de Paris and *Pelargonium x hortorum* is commercially available or available from botanical gardens.
Figure 3:
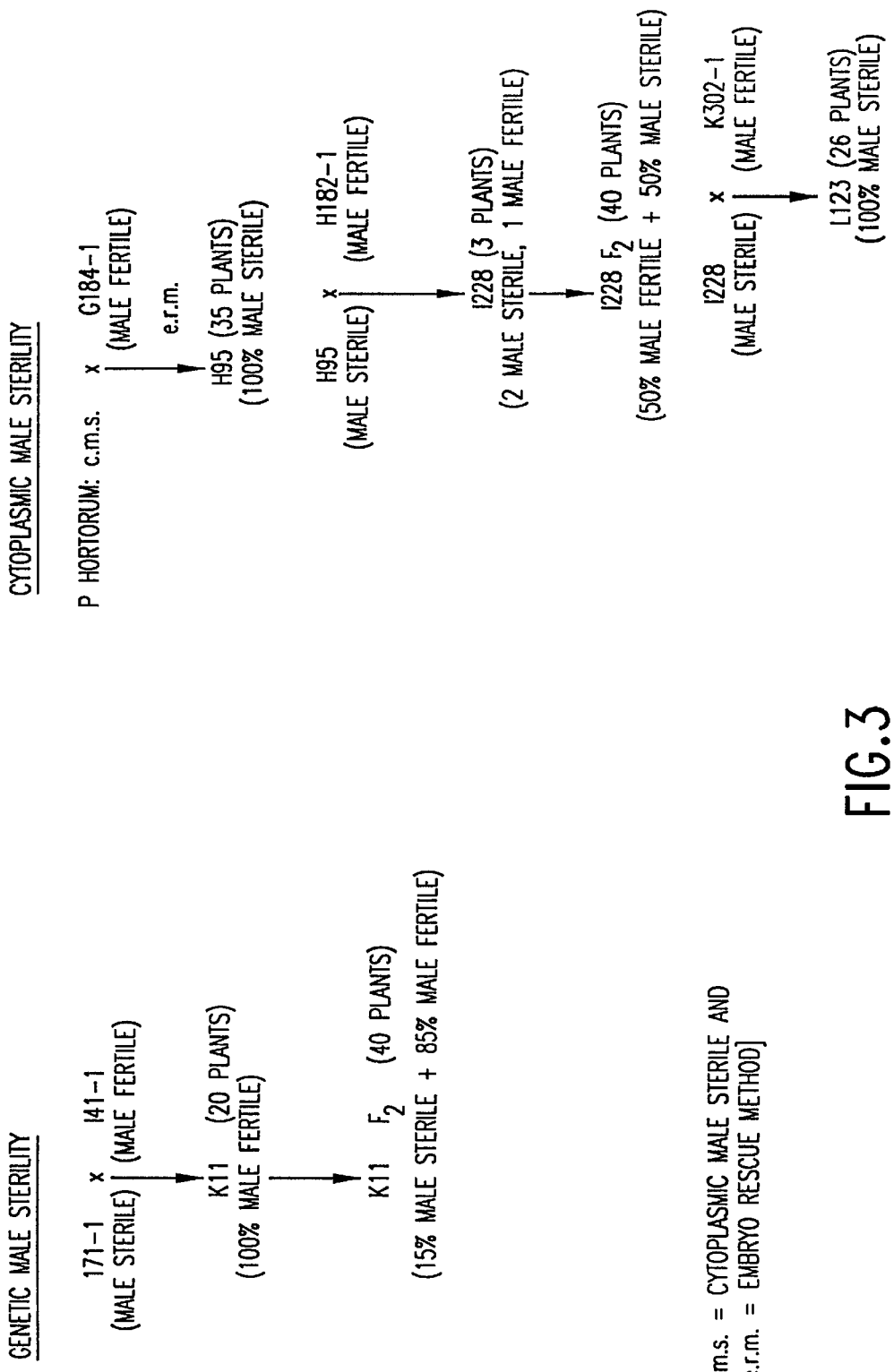
FIG. 3 shows two examples of breeding programmes initiated for the introduction of male sterility into *Pelargonium peltatum*. The parents in each of these 2 schemes were produced during an earlier breeding programme, in which the parent plants were *Pelargonium peltatum* and Balcon Princess, the genetic material of which is commercially available, or obtainable from botanical gardens. The *Pelargonium x hortorum* genetic material used in this programme is also commercially available.

An Example for the production of rose coloured *P. peltatum* and for the production of deeprose and scarlet coloured *P. peltatum* and of male sterility in *Pelargonium peltatum* is given by the Breeding Schemes 2, 3 and 4 as illustrated in FIGS. 1, 2, and 3, respectively.

EXAMPLE 3

Petal Chromatography

To determine the presence or absence of specific anthocyanidins in the petals of plants coming out of the breeding programme, chromatography may be performed on extracts of the petals.

The petals of approximately 10 flowers from each plant to be tested are placed in 2 ml of 2N HCl. The tubes are placed in the refrigerator for 24 hours and then placed in a glycerol bath at 100° C. for 40 minutes. The liquid is then removed from the tubes and centrifuged for 8 minutes at 2500 rpm. The upper layer is removed, 2 drops of isoamyl alcohol added and shaken for 1½ minutes. The sample is then divided between two different thin layer cellulose plates and the two plates chromatographised using the following solutions:
a) 50 cc isopropanol
   50 cc 2N HCl values (decimal scale) determined by the intensity and size of the spots obtained, the total value of all anthocyanidins present being 10.

For example, plant number I13-1 is the $F_6$ generation resulting from the self-pollination of plant D2623 of Breeding Schemes 2 and 3.

TABLE 1

RESULTS OF CHROMATOGRAPHY OF *P PELTATUM* PETAL EXTRACTS

| PLANT NO | COLOUR DESCRIPTION | RHS COLOUR CHART | PELARGONIDIN | CYANIDIN | PAEONIDIN | DELFINIDIN | MALVIDIN |
|---|---|---|---|---|---|---|---|
| I13-1 | deep lilac (= mauve) | 74C | | + | | 2 | 8 |
| I14-1 | deep lilac (= mauve) | 74C | | + | | 2 | 8 |
| I81-1 | deep salmon | 55B | 4 | + | 3 | + | 3 |
| I95-1 | deep salmon | 55B | 3 | + | 3 | 2 | 2 |
| I140-1 | light scarlet | 44B | 4 | | 4 | + | 2 |
| I126-1 | scarlet | 44A | 4 | | 4 | | 2 |
| I198-1 | scarlet | 44A | 5 | + | 5 | | + |
| I127-1 | deep scarlet | 44A | 5 | | 2 | | 3 |
| I140-9 | rose | 57B | 3 | | 4 | + | 3 |
| I140-4 | deep rose | 57A | 4 | | 3 | + | 3 | wherein the figures are values relative to each other
+ means only a trace

TABLE 1A

Results of Chromatography of *P. pelatatum* petal extract.

| Plantnr. | Colour description | pelargonidin | cyanidin | paeonidin | delfinidin | malvidin |
|---|---|---|---|---|---|---|
| L382-1 | red lilac | | 1 | 1 | 2 | 6 |
| L432A-1 | red lilac | | 1 | 1 | 2 | 6 |
| L462-3 | deep salmon | 2 | | 4 | | 4 |
| L471-1 | deep salmon | 2 | 1 | 2 | 3 | 2 |
| L480-1 | deep salmon | 3 | | 4 | | 3 |
| L514-1 | salmon | 2 | + | 4 | + | 4 |
| L532-2 | salmon orange | 5 | | 4 | | 1 |
| L569-1 | deep salmon orange | 4 | | 4 | | 2 |
| L219-1 | deep Paeonidin Malvidin rose | 2 | + | 4 | 1 | 3 |
| L221-1 | Paeonidin rose | + | + | 5 | 1 | 4 |
| L221-2 | Paeonidin Malvidin rose | + | + | 5 | 1 | 4 |
| L558-2 | Paeonidin rose | 1 | + | 1 | + | |
| L558-5 | deep Paeonidin Malvidin rose | 2 | 1 | 3 | 1 | 1 |
| L559-2 | Paeonidin Malvidin rose | | + | 4 | 1 | 5 |
| L591-2 | deep scarlet | 2 | + | 5 | 1 | 2 |
| L593-4 | Malvidin scarlet | 3 | + | 6 | + | 1 |
| L596-1 | scarlet | 3 | | 6 | | 1 | b) 15 cc aqua dest
   45 cc conc acetic acid
   4.5 cc 32% HCl

After 4 to 5 hours the plates are removed from the baths and the positions of the different spots, corresponding to the anthocyanidins, is analysed. The results of such a chromatography on extracts of petals from plants obtained in a breeding programme in which the genetic material of the parents is either commercially available or obtainable from botanical gardens, are shown in Table 1. The quantitative results given for the individual anthocyanidins are relative

EXAMPLE 4

Production of Scarlet Coloured Flowers in *P. peltatum* (Breeding Scheme 5)

The parents of the breeding programme were selected from inbred lines of the existing breeding programme of *P. peltatum* with white, salmon and lilac flowers and *P. hortorum* lines with pelargonidine and peonidine (scarlet and deeprose flowers). The zygotes resulting from these crosses had to be removed from the plant and grown in culture (as per example 1). These crosses were backcrossed again with

*P. peltatum* lines. Again the embryo rescue method had to be carried out to get a new F1 progeny. Some of the thus obtained F1 plants had the desired characteristics (scarlet flower). They were used in further backcrosses which succeeded in the natural way. The last step was to cross plants with the darkest colour possible (scarlet L193 and Paeonidin Malvidin rose L191).

This F1 progeny segregated only in dark colours (scarlet and Paeonidin Malvidin rose). The F3 progeny (after self-pollinating twice) was uniform for the scarlet colouring.

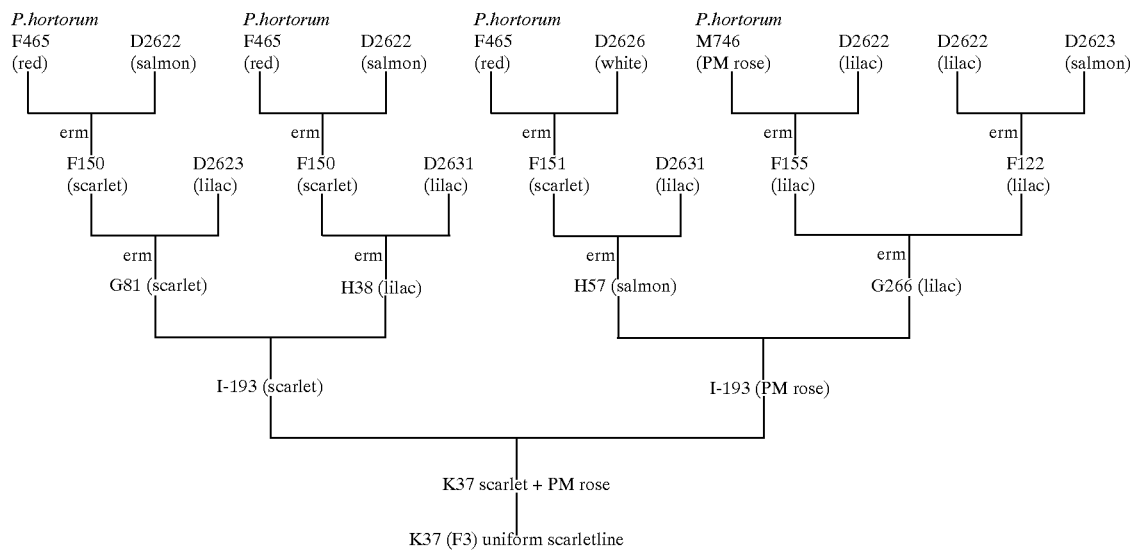

BREEDING SCHEME 5
Production of scarlet coloured flowers in *P. peltatum*

Wherein erm = embryo rescue method and PM rose = Paeonidin-Malvidin-rose

What is claimed is:

1. A diploid seed propagatable *Pelargonium peltatum* plant whose petals express at least one of the anthocyanidins pelargonidin or paeonidin.
2. A plant according to claim 1 wherein the chromatographically determined content of the pelargonidin and paeonidin is at least 1% of the total anthocyanidin content.
3. A plant according to claim 2 wherein the chromatographically determined content of the pelargonidin and paeonidin is at least 5% of the total anthocyanidin content.
4. A plant according to claim 3 wherein the chromatographically determined content of the pelargonidin and paeonidin is at least 10% of the total anthocyanidin content.
5. A plant according to claim 4 wherein the chromatographically determined content of the pelargonidin and paeonidin is at least 25% of the total anthocyanidin content.
6. A plant according to claim 1 whose petals express both pelargonidin and paeonidin.
7. A plant according to claim 1 further displaying at least one characteristic selected from the group consisting of:
   a) day-neutrality; and b) white spot in the center of the flowers.
8. Seeds produced by the plant of claim 1.
9. Seeds produced by the plant of claim 7.
10. Propagating material of the plant of claim 1.
11. Propagating material of the plant of claim 7.
12. A diploid seed propagatable *Pelargonium peltatum* plant containing a factor resulting in male sterility.
13. A plant according to claim 12 wherein the male sterility is genetic male sterility.
14. A plant according to claim 13 further expressing in its petals at least one of the anthocyanidins selected from the group consisting of pelargonidin and paeonidin.
15. A plant according to claim 14 wherein the chromatographically determined content of the pelargonidin and paeonidin is at least 1% of the total anthocyanidin content.
16. A plant according to claim 15 wherein the chromatographically determined content of the pelargonidin and paeonidin is at least 5% of the total anthocyanidin content.
17. A plant according to claim 16 wherein the chromatographically determined content of the pelargonidin and paeonidin is at least 10% of the total anthocyanidin content.
18. A plant according to claim 17 wherein the chromatographically determined content of the pelargonidin and paeonidin is at least 25% of the total anthocyanidin content.
19. A plant according to claim 13 further expressing on its petals both pelargonidin and paeonidin.
20. A plant according to claim 13 further expressing at least one character selected from the group consisting of:
   a) day-neutrality; and b) white spot in the center of the flowers.
21. Seed produced by the plant of claim 13.
22. Seed produced by the plant of claim 14.
23. Seed produced by the plant of claim 20.
24. Propagating material of the plant of claim 13.
25. Propagating material of the plant of claim 14.
26. Propagating material of the plant of claim 20.
27. A seed propagated diploid *Pelargonium peltatum* plant comprising:
   a) a factor resulting in male sterility;
   b) at least one of the anthocyanidin pigments, pelargonidin and paeonidin, expressed in the plant petals;
   c) seed produced by said plant and
   d) propagating material thereof.

* * * * *